United States Patent
Nadal et al.

[11] Patent Number: 6,152,931
[45] Date of Patent: Nov. 28, 2000

[54] MEDICAL DEVICE COMPRISING A ROD EQUIPPED WITH A MEANS FOR ABSORBING AXIAL STRESSES

[75] Inventors: Guy Nadal, Poitiers; Gilles Bovyn, Saint-Brieuc, both of France

[73] Assignee: B. Braun Celsa, France

[21] Appl. No.: 09/249,307

[22] Filed: Feb. 12, 1999

[30] Foreign Application Priority Data

Feb. 16, 1998 [FR] France ................................ 98 01835
Apr. 15, 1998 [FR] France ................................ 98 04685

[51] Int. Cl.[7] .................................................. A61M 5/165
[52] U.S. Cl. ........................... 606/108; 606/200; 604/280
[58] Field of Search .................................. 606/108, 200; 604/280, 281, 282, 283, 523

[56] References Cited

U.S. PATENT DOCUMENTS

| | | | |
|---|---|---|---|
| 4,593,690 | 6/1986 | Sheridan et al. | 128/207.15 |
| 4,852,564 | 8/1989 | Sheridan et al. | 128/202.27 |
| 4,871,356 | 10/1989 | Haindl et al. | 604/247 |
| 5,026,377 | 6/1991 | Burton et al. | 606/108 |
| 5,146,925 | 9/1992 | Snow | 128/658 |
| 5,151,105 | 9/1992 | Kwan-Gett | 623/1 |
| 5,300,086 | 4/1994 | Gory et al. | 606/200 |
| 5,348,541 | 9/1994 | Lyell | 604/164 |
| 5,391,183 | 2/1995 | Janzen | 606/123 |
| 5,498,250 | 3/1996 | Prather | 604/280 |
| 5,534,007 | 7/1996 | St. Germain et al. | 606/108 |
| 5,713,907 | 2/1998 | Hogendijk et al. | 606/108 |
| 5,749,918 | 5/1998 | Hogendijk | 623/1 |
| 5,762,615 | 6/1998 | Weier | 600/585 |
| 5,817,101 | 10/1998 | Fiedler | 606/108 |

FOREIGN PATENT DOCUMENTS 2715827   7/1994   France.

*Primary Examiner*—Paul J. Hirsch
*Assistant Examiner*—Michael B. Priddy
*Attorney, Agent, or Firm*—Rothwell, Figg, Ernst & Manbeck

[57] ABSTRACT

The invention relates to a device for medical use which is capable of being introduced into a duct of a living human or animal body, said device comprising a biocompatible flexible rod which has an axis along which it extends, free of stress, in a rectilinear manner, said rod having a length along this axis, a distal end and a proximal end. This device is characterised in that in order that the rod should remain substantially at a specific implantation location in the duct it is equipped with at least one means for absorbing axial stresses which is disposed along the axis thereof and is distinct therefrom whilst being connected thereto, such that its proximal end is not substantially displaced axially once the rod has reached the specific implantation location in the duct.

10 Claims, 10 Drawing Sheets

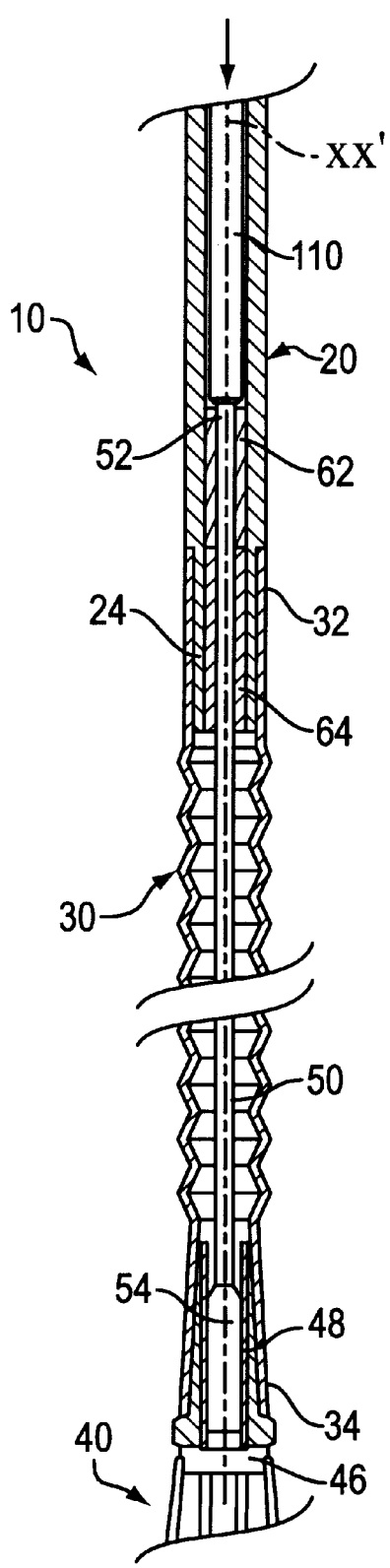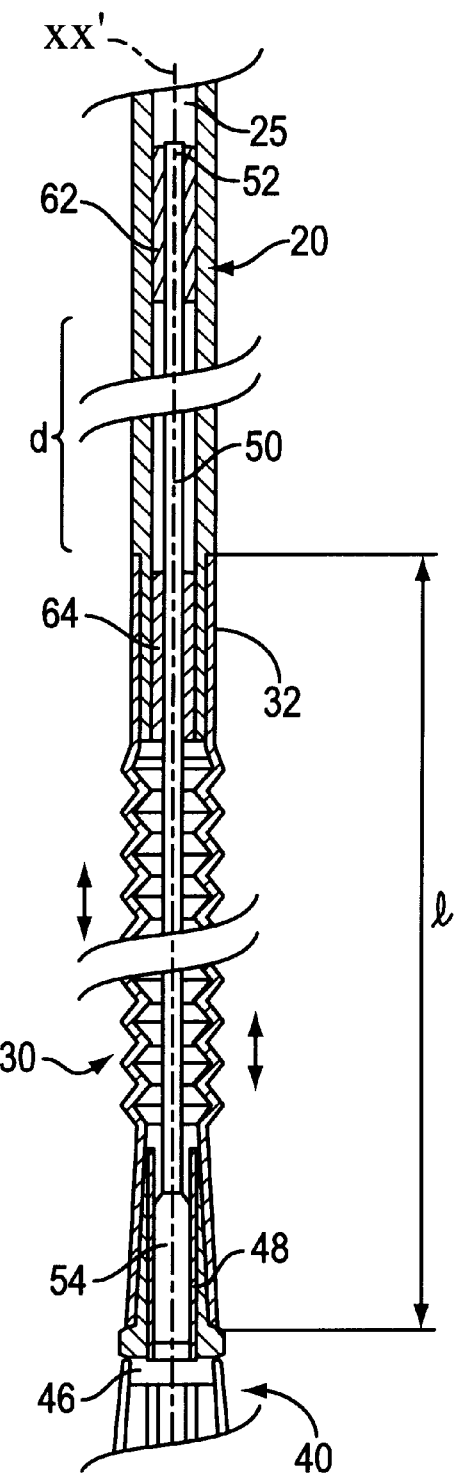
FIG. 2
FIG. 3

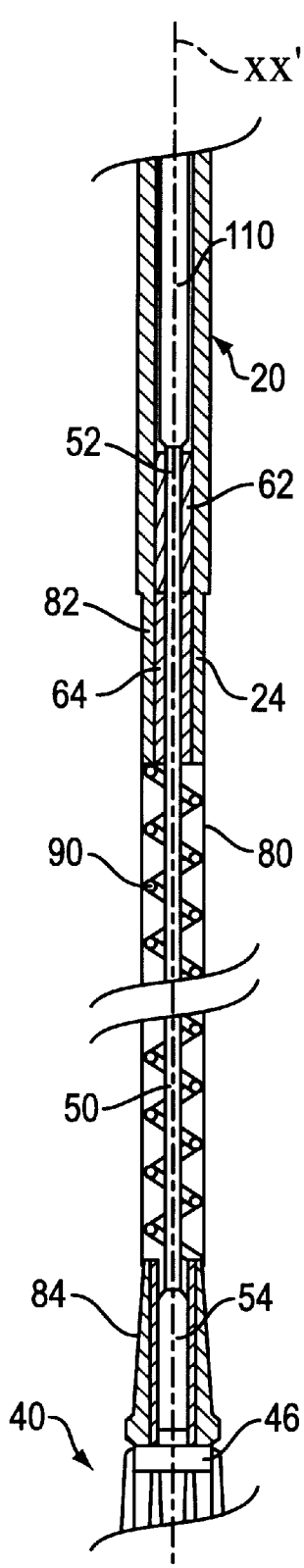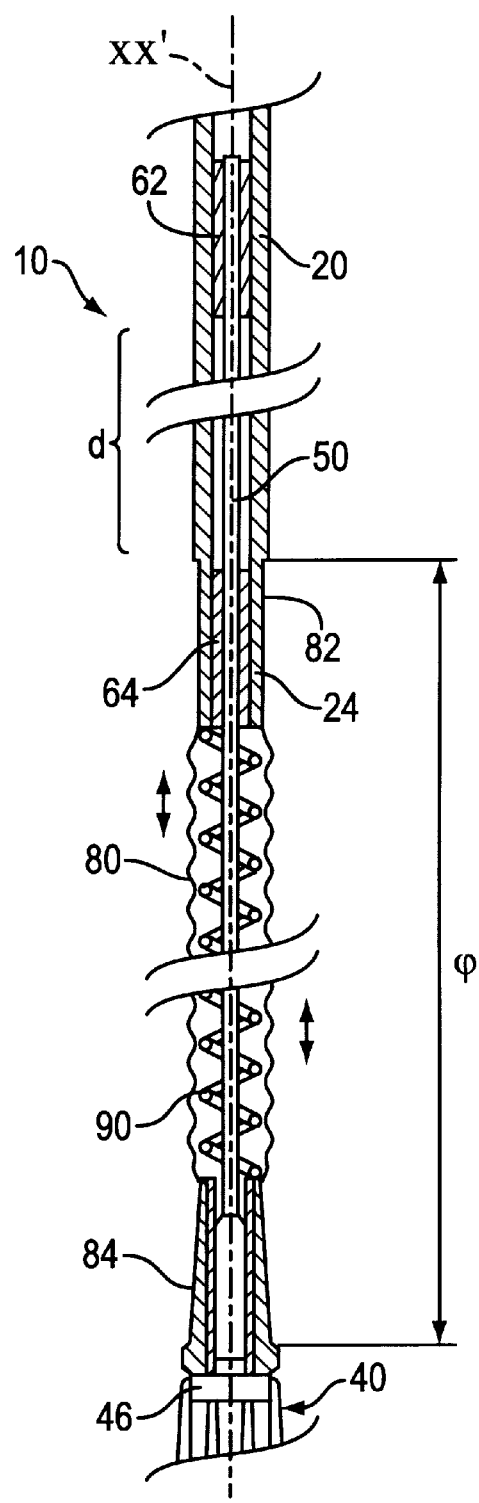
FIG. 4
FIG. 5

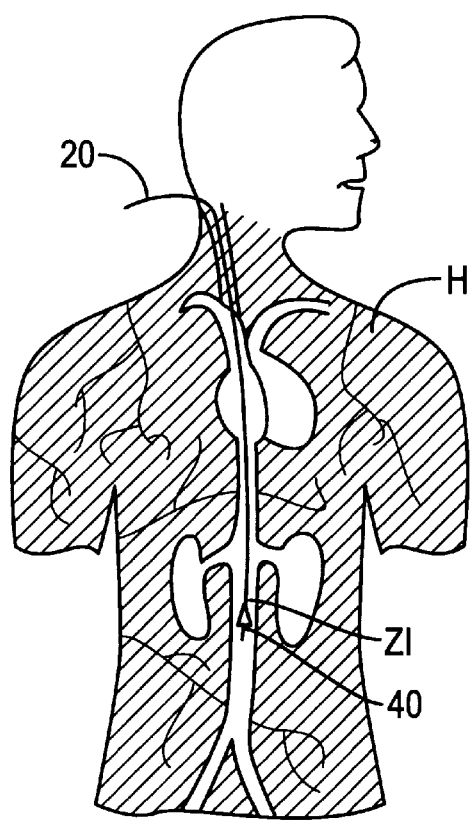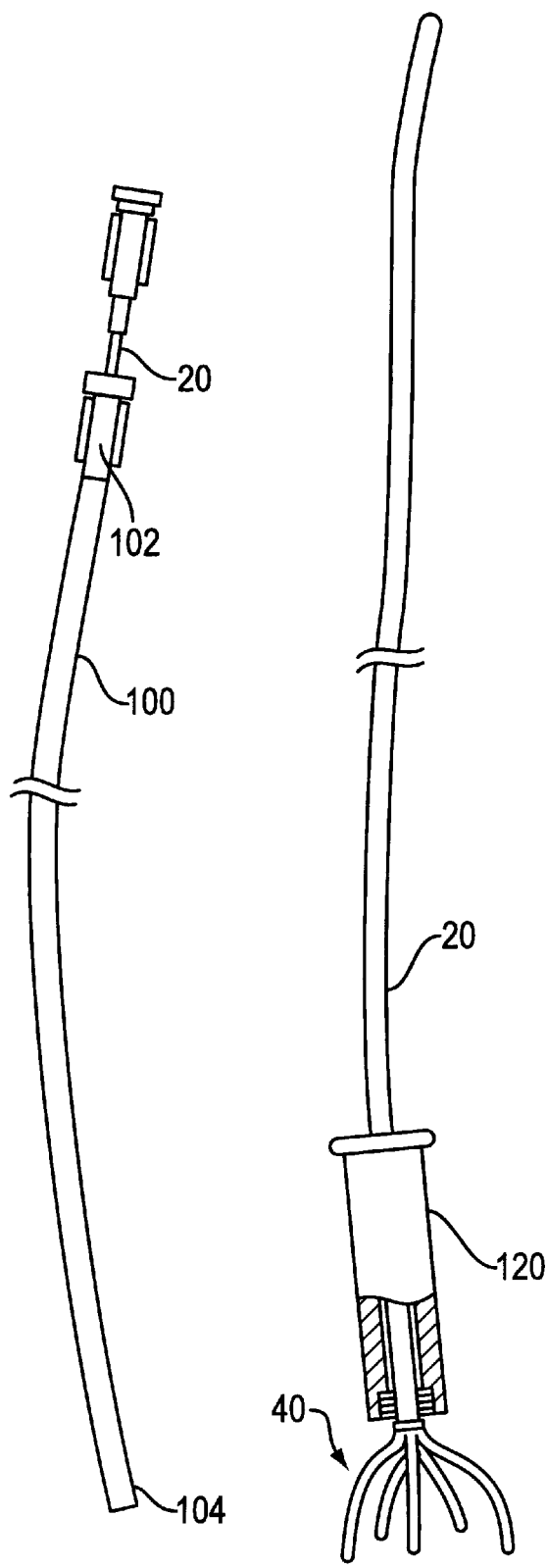
FIG. 8  FIG. 9  FIG. 10

MEDICAL DEVICE COMPRISING A ROD EQUIPPED WITH A MEANS FOR ABSORBING AXIAL STRESSES

The invention relates to the field of devices for medical use which can be implanted in an anatomical duct.

BACKGROUND OF THE INVENTION

More precisely, it relates to a device comprising a flexible biocompatible rod which has an axis along which it extends, free of stress, in a rectilinear manner, said rod having a length along this axis, a distal end and a proximal end.

This type of rod currently presents certain drawbacks and is not entirely satisfactory, both for the practician manipulating it and for the patient inside whose body it is placed. In particular, in the case of movement of the patient (moving from the sitting position to the lying position, even to the foetal position, and vice versa), the rod tends to adapt to the configuration of the duct (curvature) inside which it is introduced and to be displaced therein in such a way that its ends do not remain in place, which can be inconvenient. Thus with this type of rods there is a problem of stability and of keeping them in place when they are positioned at a specific implantation location inside the body of a patient.

SUMMARY OF THE INVENTION

In order to solve this, it is proposed that the rod be equipped with at least one means for absorbing axial stresses which is disposed along the axis of said rod and which is distinct therefrom whilst being connected thereto, such that the proximal end of the rod is not substantially displaced axially once said rod has reached the specific implantation location in the duct.

It is specified here that any rod will be "rectilinear" which at rest has a straight general direction of extension and which therefore does not present locally, at least at the location of its means for absorbing stresses, a marked curvature (bend) which could serve as a shock absorber (as in FR-A-2 715 827).

In relation to such a rod, the invention relates in particular to devices for temporary implantation of a vascular implant, such as a blood filter. Such a filter is in particular described in EP-A-521 522 or U.S. Pat. No. 5,634,942.

Experience has shown that at the time of implantation of an implant, and in particular a blood filter, because of the blood flow the implant is displaced axially in the vessel when it has no means for attachment to the wall of the vessel. It has also been remarked that during the period of temporary implantation of the implant this latter can, due to the movements and changes of position of the patient, be displaced in the duct and even be torn away if it has begun to be covered with aggregation of cells.

Thus the invention relates to a device for putting into place in a temporary manner inside an anatomical duct of a patient an implant comprising a radially expansible structure, and in particular a blood filter, said device comprising in particular the rod as set out above.

When it is required to put the implant temporarily in place in the body of the patient, it may be wished, after the rod has been introduced into the interior of the anatomical duct of the patient, to place below the patient's skin the proximal end of the rod at the other end of which the implant is disposed. In this case, the adaptation of the curvature of the rod in the case of movement of the patient may also cause a painful displacement of the proximal end thereof at the point where it is connected to a subcutaneous locating part (see EP-A-521 222), even a part intended to ensure injection/sample-taking operations (via an implantable chamber, as in FR-A-2 697 995).

In order to solve this, the means, or at least one of these means, for absorbing the axial stresses can be disposed towards the proximal end of the rod where this latter is connected to the subcutaneous part, which latter is therefore locatable by palpation through the patient's skin.

Always with the aim of solving the problem presented above, the invention provides in particular that the locating part is equipped with said means for absorbing stresses, in particular in the form of a device with a piston and/or possibly a spring.

According to a complementary aspect, the means for absorbing axial stresses may comprise a bellows which can lengthen or shorten axially. This simple solution guarantees a progressive and continuous absorption, can adapt equally well to a solid rod as to a hollow one, and can be positioned at any location whatsoever on the rod.

According to an alternative, the means for absorbing stresses can comprise a spring.

According to another alternative which may be complimentary to the two preceding ones, the means for absorbing axial stresses can comprise a piston. This solution also offers transverse retention of the means for absorbing stresses.

In particular if the implant is a filter comprising a head from which radially expansible fingers extend, the means for absorbing axial stresses can be fixed towards the distal end of the rod. Thus the shock absorbing effect is concentrated in a critical zone, that is to say the zone where the implant is placed. Thus the stresses which are exerted on the implant are immediately compensated by the absorption means, and thus these stresses are not (or only very little) transmitted to the rod.

In order to resolve the difficulties which may occur in implanting and withdrawing the implant, the piston can comprise a second pusher rod which is mounted so as to slide in the interior of the first rod by means of this latter and connected to the implant.

In order to improve the relative sliding of the piston inside the rod, the device can also comprise a guiding and stop system in order to limit the axial displacement in the interior of the rod.

In particular, this system can comprise a first ring fixed inside the first rod, the internal diameter of this first ring being slightly greater than the external diameter of the piston, and a second ring (or protrusion) connected to the piston, the external diameter of this second ring being slightly less than the internal diameter of the rod.

Independently of the problems referred to above of absorbing the axial stresses, another problem arises in relation to the use of an implantable site to connect to a device for medical use which is capable of being introduced into a duct of a living human or animal body, such as a catheter.

For information, it will be noted that the "distal" end of the elements of the device designates the end which must implanted most deeply in the body of the patient, the "proximal" end being the opposite end situated close to the surface of the skin (even on the exterior).

BRIEF DESCRIPTION OF THE DRAWINGS

The invention and implementation thereof will become even more clearly apparent with the aid of the following description with reference to the drawings, in which:

FIGS. 2 and 3 are sectional views of details of the device according to the FIG. 1, FIGS. 4 and 5 are sectional views of details of a variant of the device according to FIG. 1, FIGS. 6 and 7 are sectional views of a details of another variant of the device according to FIG. 1, FIG. 8 is a diagrammatic sectional view of the body of a patient in which the device according to FIG. 1 is implanted, FIGS. 9 and 10 show certain of the principal means used for positioning or withdrawing the device according to the invention.

DETAILED DESCRIPTION OF THE PREFERRED EMBODIMENT

As one of the particular objects of using this device is to be able to improve the conditions of implantation of temporary blood filters, the invention will only be described below within the scope of such an application, even though it must be clear than it can be applied to other medical implants, which may or may not be vascular (stents for example).

Figure 1:
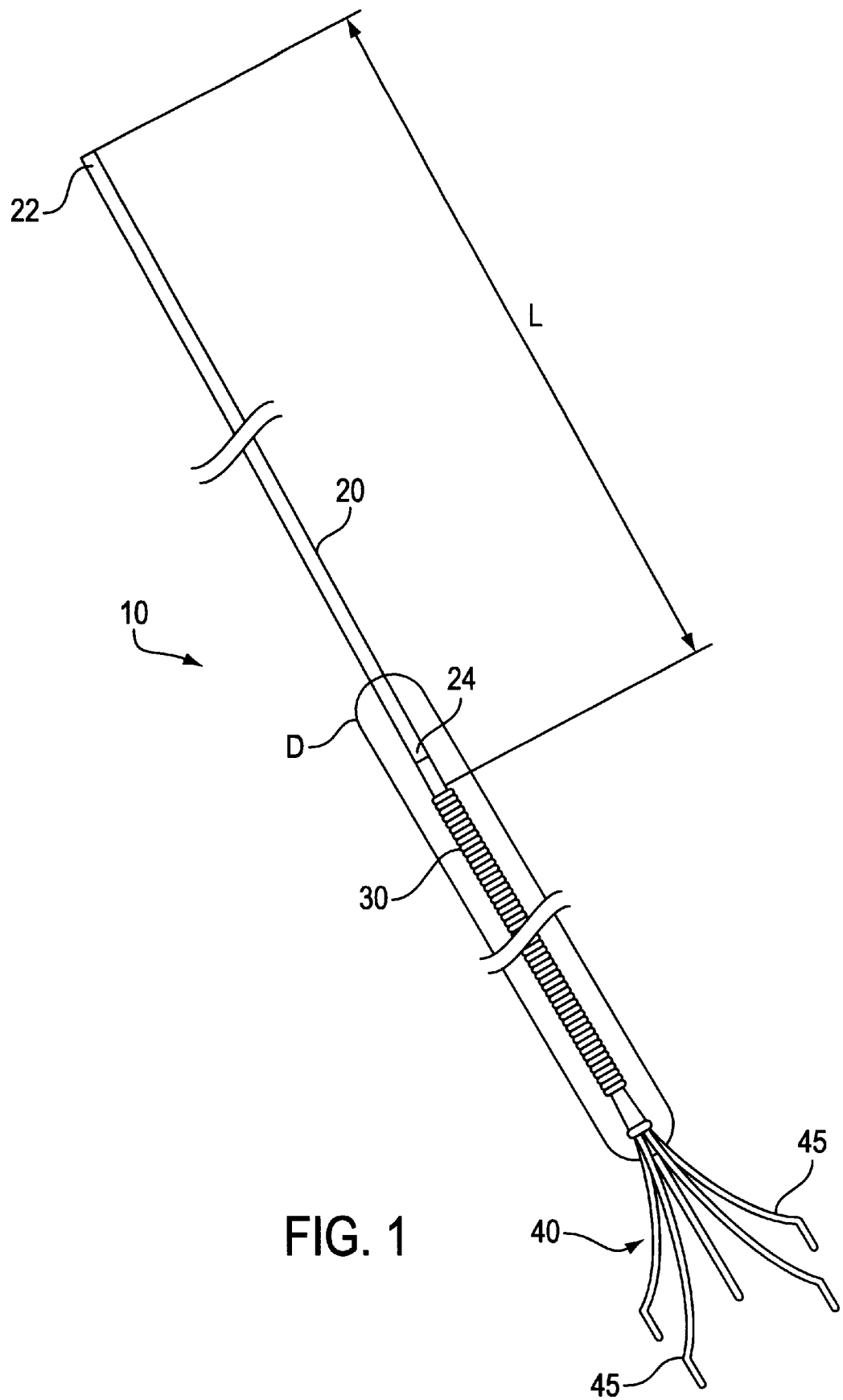
FIG. 1 is a general view of a device according to the invention.

Thus, FIG. 1 illustrates in its entirety a temporary filtration unit 10 which has a substantially rectilinear general axis xx' and which can be put in place by the subcutaneous route ("SELDINGER" method) or by stripping.

This device 10 essentially comprises a biocompatible rectilinear flexible rod 20 having an axis xx' and a length L along this axis, with a proximal end 22 and an opposite distal end 24. This rod 20 may be solid or may preferably have an internal passage 25 so that it thus forms a catheter. FIGS. 2 and 5 show the detail D in FIG. 1.

Figure 15:
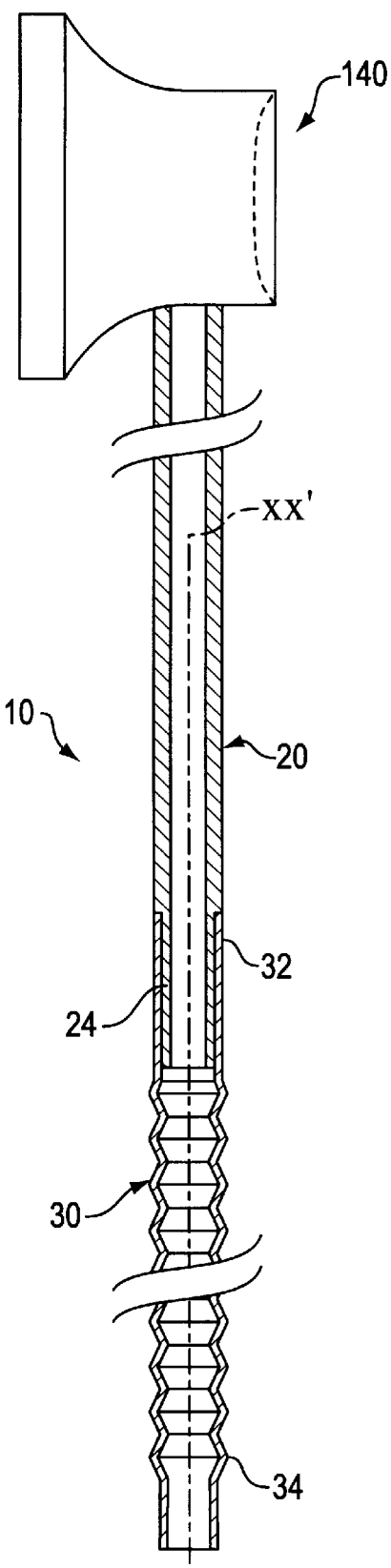
FIG. 15 is another variant.

At its proximal end 22, the rod 20 is here connected to a subcutaneous part 70 (see FIGS. 6 and 7) which is substantially fixed in position, also known as a "locating bulb", which, once said part 70 is entirely buried below the skin of the patient, for example in the subclavian zone, makes it possible to facilitate location of the proximal end of the rod 20 by palpitation through the skin (see (EP-A-521 522). If the rod 20 is hollow, as an alternative, the subcutaneous part 70 may be an implantable chamber for distribution of a treatment product, such as is described in FR-A-2 697 995. This variant is illustrated in FIG. 15.

The device 10 also comprises a bellows 30, preferably made from silicone, which has a proximal end 32 and a distal end 34. Its proximal end 32 is fixed, for example by sticking or crimping, around the distal end 24 of the rod 20. This bellows 30 has an initial length (l) in its free state (state in which it is not compressed nor stretched axially) along the axis xx' of the rod 20 equal to approximately one tenth of the total length L of the latter, that is to say between approximately 5 and 15 centimeters, this bellows 30 being capable of extending or contracting axially up to approximately 50% of its initial length. The bellows 30 is preferably liquid-tight and is of the type which is elastically deformable, that is to say that after having an axial compression or traction stress applied on its two ends it returns by itself into its rest position where it has its initial length (l).

At its distal end 34, the bellows 30 is also fixed to a blood filter 40 made from biocompatible metal (stainless steel) which in the opened position has a general shape of a conical corolla. This filter 40 comprises fingers 45 lacking any means for attachment (hooks for example) to the vessel and all coming out of a common head 46 around which the bellows 30 is fixed by means of a ring 48. These fingers 45 may in particular be automatically radially expansible, free of stress, in order to have a natural tendency to open out until their free end comes into contact with the vessel wall.

The device 10 likewise comprises a second rod 50 which acts as a piston and pusher and is disposed in the interior of the rod 20 in such a way as to be able to slide longitudinally in the interior thereof. This pusher rod 50 has a distal end 54 fixed to the head 46 of the filter 40 and a proximal end 52 around which is crimped a first ring 62 which co-operates with a second ring 64 fixed in the interior of the rod 20 at its distal end 34. These two rings 62 and 64 serve to guide the pusher rod 50 in the interior of the rod 20 and to limit its axial displacement (d) by acting as a stop when the bellows is compressed or extended.

As the filter 40 is intended to be implanted in the interior of a blood vessel it has been observed in the devices according to the prior art that it was particularly subject to mechanical stresses caused by the movements of the patient. Such stresses tend to propagate along the rod 20. The locating part 70, like the filter 20 itself, can therefore be subject to a displacement which is not very comfortable for the patient and risks giving rise to accompanying complications.

Thus the bellows 30 enables these axial stresses to be absorbed and untimely displacements of the filter or of the locating part 70. As can be seen in FIG. 3, where it is considered that the filter is implanted in the vessel (see also FIG. 8), the bellows 30 is in a free state in which the pusher 50 can be displaced axially. It can therefore stretch or compress axially along with the movements of the patient, without the filter 40 or the proximal end 22 of the rod 20 being displaced axially, in particular when the filter 40 is covered with an aggregate of cells or when it is partially jammed. The displacement of the bellows 30 obviously gives rise to displacement of the pusher rod 50 in the interior of the rod 20, which contributes to an improvement in the absorption of axial stresses whilst preventing them from being transmitted to the first rod 20. It may therefore be noted that this second pusher rod 50 in itself constitutes a means for absorbing axial stresses in the form of a piston.

FIGS. 4 and 5 show a variant of the device according to FIGS. 2 and 3 which can be used at one and/or the other of the ends of the rod 20. In this solution the means for absorbing stresses comprises an impervious sheath 80 (or sleeve) made from a very fine biocompatible material which can in particular be deformed and fold on itself without being perforated, such as silicone, and a helical spring 90. The sheath 80 is fixed, like the bellows 30, to the head 46 of the filter 40 on the one hand and to the distal end 24 of the rod 20 on the other hand, in such a way as to render the device 10 impervious to the fluid circulating in the vessel. The spring 90 is mounted in the interior of the sheath 80 and surrounds the pusher rod 50 which is equipped with a ring 62. This spring 90 is supported, in a state where it is at least partially compressed axially (particularly at the time of implantation as illustrated in FIG. 4) on the one hand against the distal end 24 of the rod 20 and on the other hand against the extension 48 of the head of the filter. The assembly comprising the sheath 80 and the spring 90 thus has the same function of absorbing stresses as the bellows 30 or the pusher rod presented above.

Figure 6:
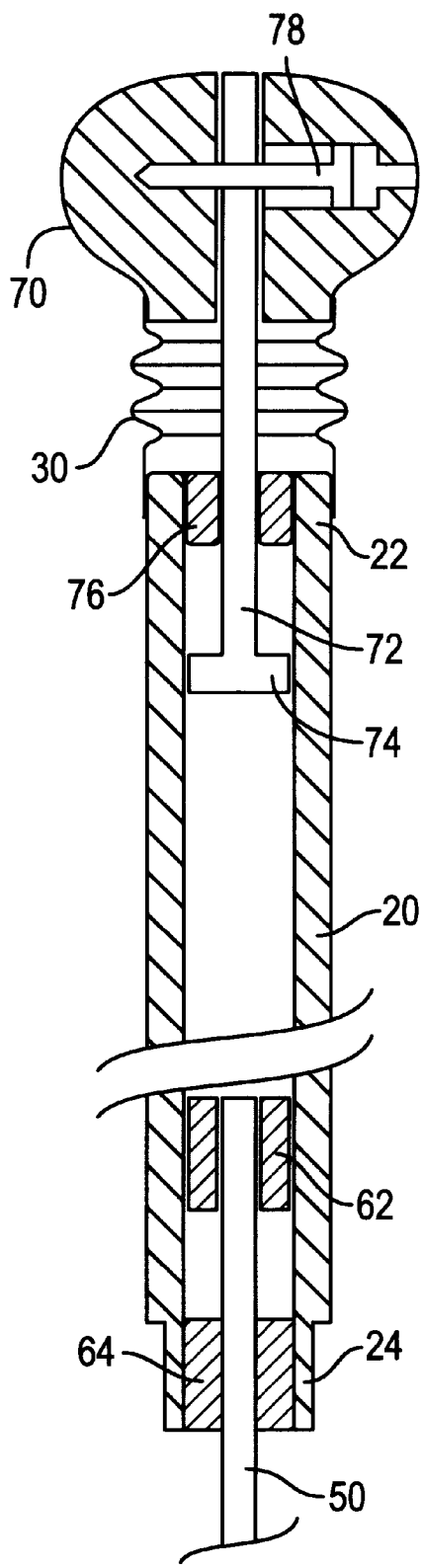
Figure 7:
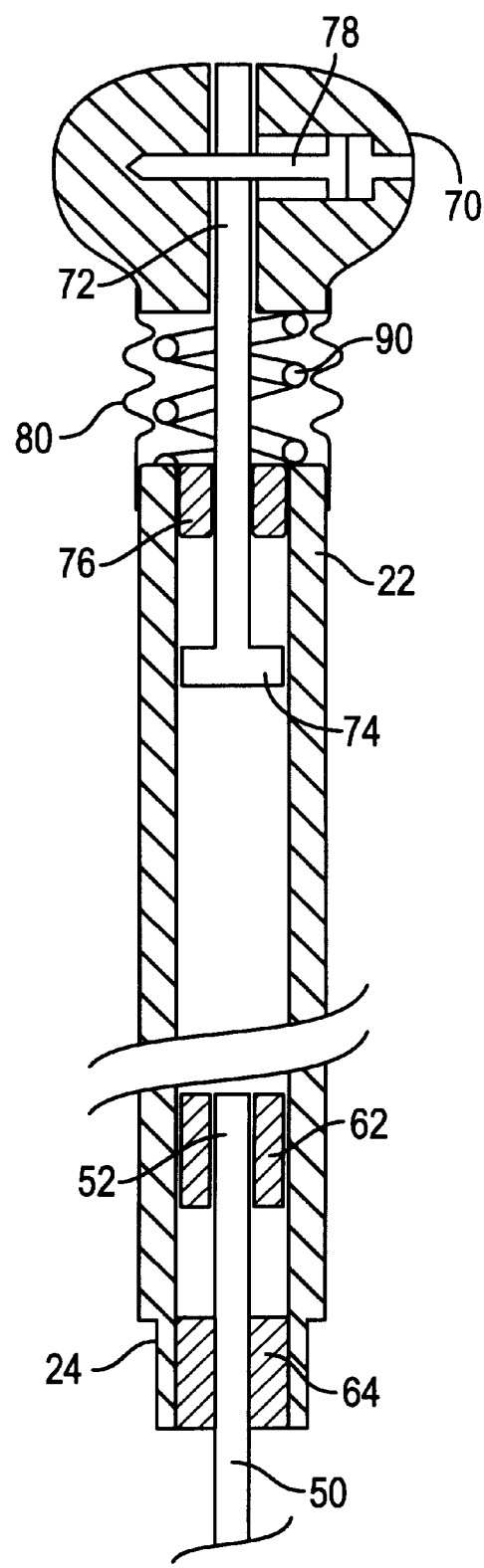

FIGS. 6 and 7 show another variant which can be used preferably in collaboration with one of the two presented above and disposed at the proximal end of the rod 20 at the point where the locating part 70 is situated. In this solution, the locating part 70 is mounted on a tube 72 which may be solid or hollow and which penetrate into the interior of the rod 20 over a certain length, for example between approximately 2 and 12 centimeters. This tube 72, acting as a piston, comprises an axial guiding and stop system comprising a projection 74 (or a first ring) which is connected to its distal end and of which the external diameter is slightly less than the internal diameter of the rod 20 co-operating with a second ring 76 which is crimped in the interior of the proximal end of the rod 20 and of the tube 72. Finally, an impervious bellows 30 connects the proximal end 22 of the rod 20 to the locating part 70 which is retained on the rod 20, for example by a nail 78.

In FIG. 7 the bellows 30 has been replaced by a combination comprising a helical spring 90 and a flexible impervious sheath 80 having the same function.

In these two variants, the axial stresses which are exerted on the distal end 24 of the rod 20 and which pass through the latter as fat as its proximal end 22 are absorbed by the piston 72 and by the bellows 30 or the spring 90. Thus the subcutaneous locating part 70 is not displaced below the patient's skin.

The implantation as far as the implantation zone (ZI) (or the withdrawal) of the blood filtration unit 40 is carried out as in FR-A-2 715 827, by the percutaneous endoluminal route, if necessary by means of an introducing conduit 100.

Once the conduit 100 is in position it serves as a guide for the positioning of the filter 40 which is usually packaged in the state where its fingers are radially confined in a sort of packaging syringe 120 (not shown) which is screwed on the proximal connector 102 of the conduit which opens outside the patient's body.

In order to cause the descent of the assembly comprising the rod 20, the filter 40 fixed to its pusher rod 50 and the bellows 30, the practician acts on the pusher rod 50 from outside the patient's body with the aid of a driver 110 (rod preferably solid and more rigid than the rod). The bellows 30 (or the sheath 80) then stretches axially whilst the filter 40 is released and expands radially, outside the conduit 100. The practician then withdraws the driver 110, cuts the rod 20 to length and fixes the part 70 to the proximal end 12 of the rod with the aid of the nail 78 before burying all of it in the patient's tissue and re-closing the access route.

Once the filter 40 is in place, the means for absorbing axial stresses (piston, bellows, spring) fulfils its function and prevents the filter and/or the part 70 from being displaced axially inside the vessel, particularly when the patient changes position.

For the sake of understanding, the scales have been disregarded in the following FIGS. 11 to 14.

Figure 11:
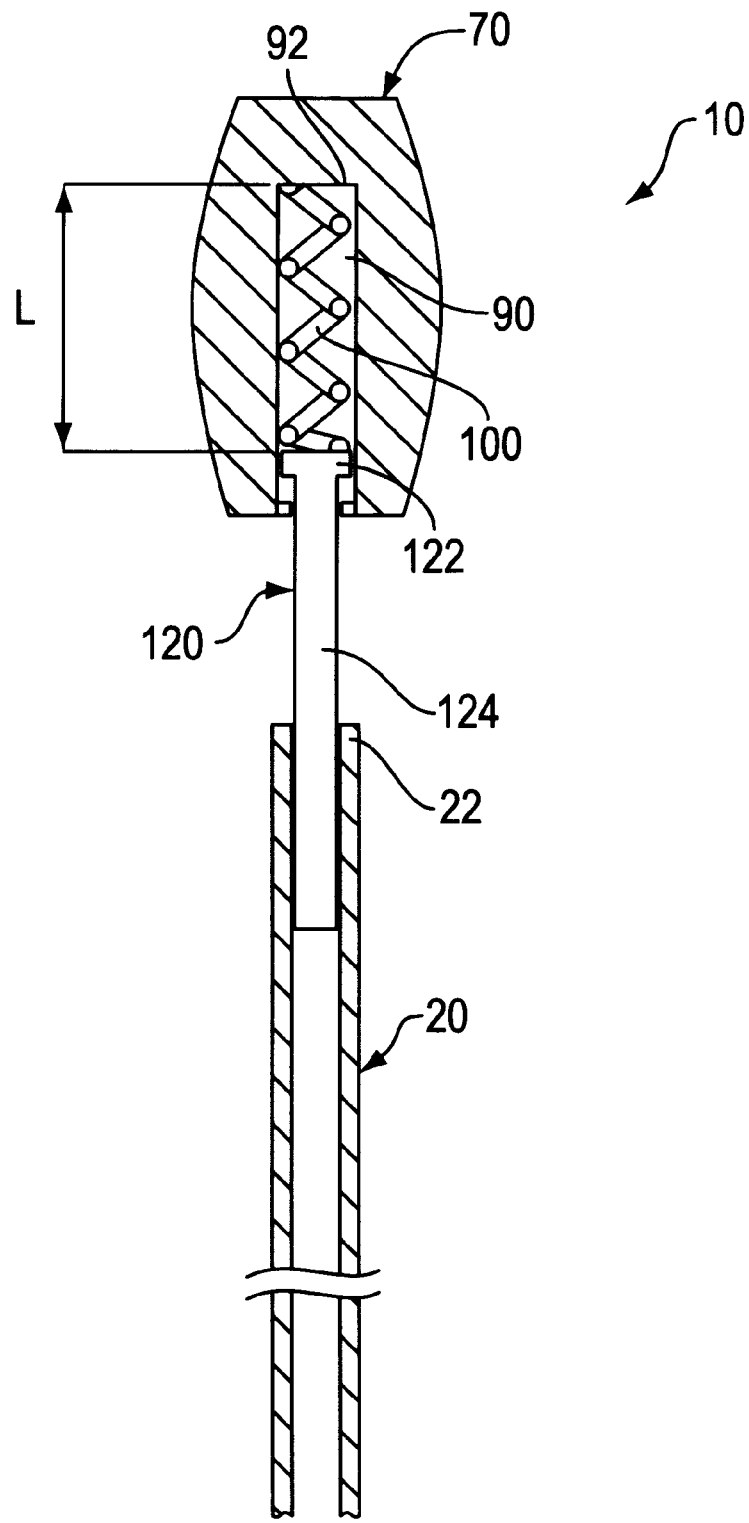
FIG. 11 is a variant of the device in which the subcutaneous locating part is equipped with a means for absorbing axial stresses.

Another variant is shown in FIG. 11 where only the proximal end of the rod 20 is shown. The subcutaneous locating part 70, preferably made from silicone, has an internal cavity 90 inside which is located a compression spring 100 which bears against the base 92 of the cavity 90 and on which a piston 120 rests which is made from biocompatible material (stainless steel) or plastics material comprising a head 122 substantially in the form of a disc and a rod 124 which is preferably solid. This rod piston 124 is fixed to the proximal end 22 of the rod 20 bearing the filter 40, for example by crimping or sticking or any other known technique. The spring 100 can be compressed axially along a course E. Thus when the device 10 is implanted in the body of the patient and the subcutaneous locating part 70 is disposed under the skin, for example in the subclavian zone, the spring 100 elastically absorbs the axial stresses which may occur by compressing as has already been explained above. Thus the locating part 70 and the filter 40 can remain at their respective implantation locations.

Figure 12:
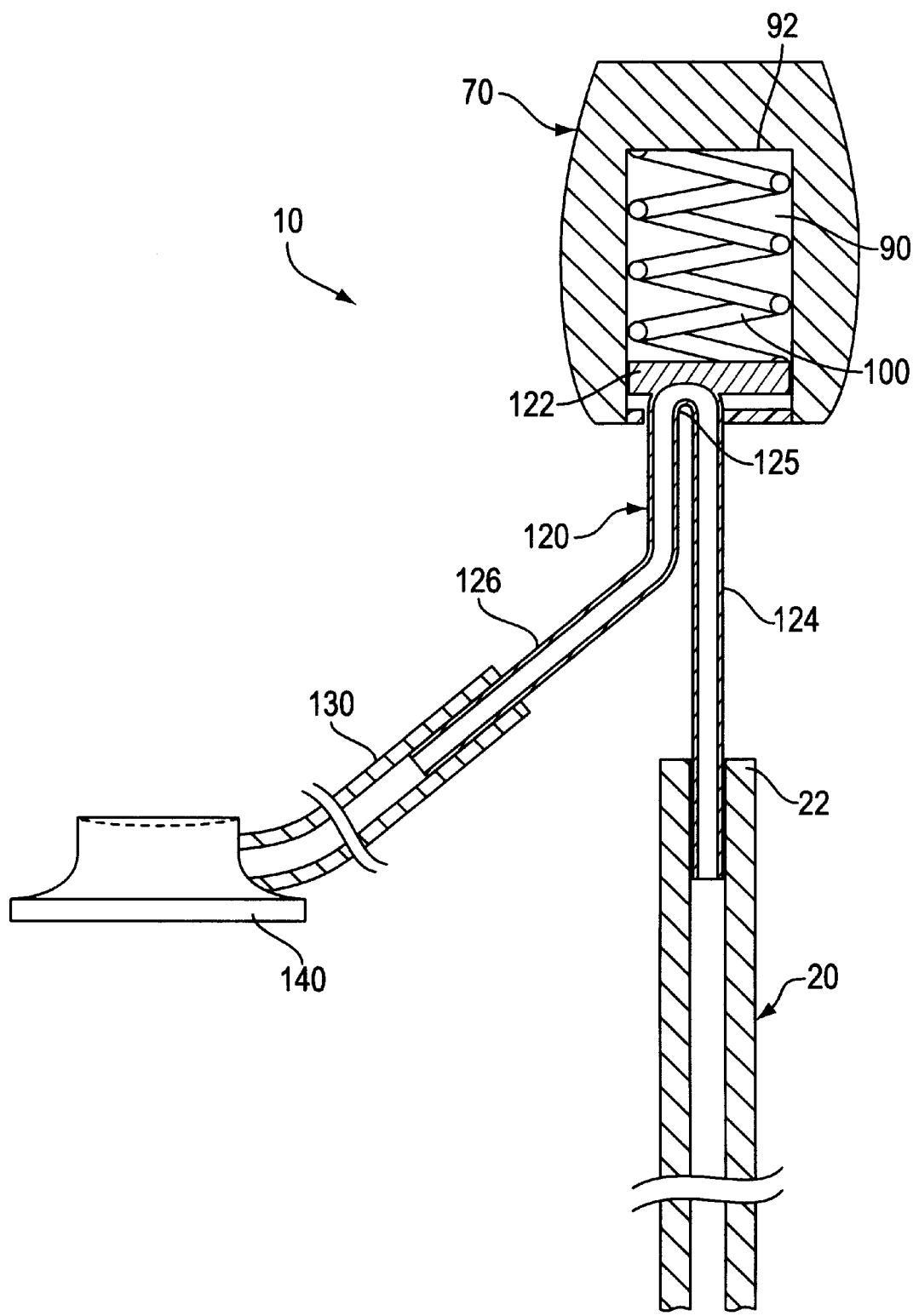
FIG. 12 is a variant of FIG. 11 in which the subcutaneous locating part also functions as a relay for an implantable site.

In FIG. 12 the locating part 70 still comprises an internal cavity 90 inside which a spring 100 is located on which rests a piston 120 connected by means of its rod 124 to the rod 20 bearing the filter 40 in the same way as previously. The piston rod 124 is hollow and forms a bend 125 (pronounced curve) at the location of the head 122 of the piston. This rod 124 is connected by a "branch 126" to a flexible catheter 130, said catheter being implanted under the patient's skin and connected to an implantable site 140 (known also as an implantable chamber) of known type (see Patent FR-A-2 697 995) likewise situated under the skin level with the rib cage. This implantable site 140 is adapted so that it is possible to introduce through its self-sealing wall 142 (for example made from silicone) a syringe containing a treatment product to be conveyed to the interior of the vessel as far as the filter, with a view for example to destroying a captured blood clot. Thus the subcutaneous locating part 70, in addition to comprising a means for absorbing axial stresses, serves as relay to an implantable site. This solution avoids having to fix the implantable site 140 directly to the proximal end 22 of the carrier rod 20 (which does not permit absorption of the axial stresses) whilst improving the comfort of the patient.

In these two variants, the means for absorbing stresses may be other than a compression spring 100, for example a leaf spring, or even a device for shock absorption by fluid (air or liquid), in which case the piston will be mounted in a sealed manner in the cavity.

It will be noted that a biocompatible flexible rod such as that shown in FIGS. 1 to 12 may be used without the presence of any implant at its distal end 22. Thus as illustrated in FIG. 15, it is possible to connect an injection catheter 20 to an implantable chamber 140 (identical to that of FIG. 12) fixed under the patient'skin and to equip said catheter 20 with a bellows 30. The changes of configuration of the vessel in which the catheter is implanted are compensated by the shock absorbing means 30 which thus permit the catheter to remain positioned at a specific implantation location inside the patient's duct. Thus its proximal end 22 is not substantially displaced axially, this being all the more true if this proximal end of the flexible rod concerned is directly fixed to the skin of the patient or if it is provided with a subcutaneous locating device such as the bulb of FIGS. 6 and 7 or 11 and 12.

Independently of the problems solved by the devices presented in FIG. 1 to 12 and 15 in relation to the absorption of axial stresses, a distinct problem is posed relating to the use of an implantable site such as that described in Patent FR-A-2 697 995. In fact there may be a problem there in connecting such an implantable site to the proximal end 22 of the rod 20, particularly when it is wished to be able to locate this proximal end 22 under the skin of the patient which ensuring a good seating at said site.

Figure 13:
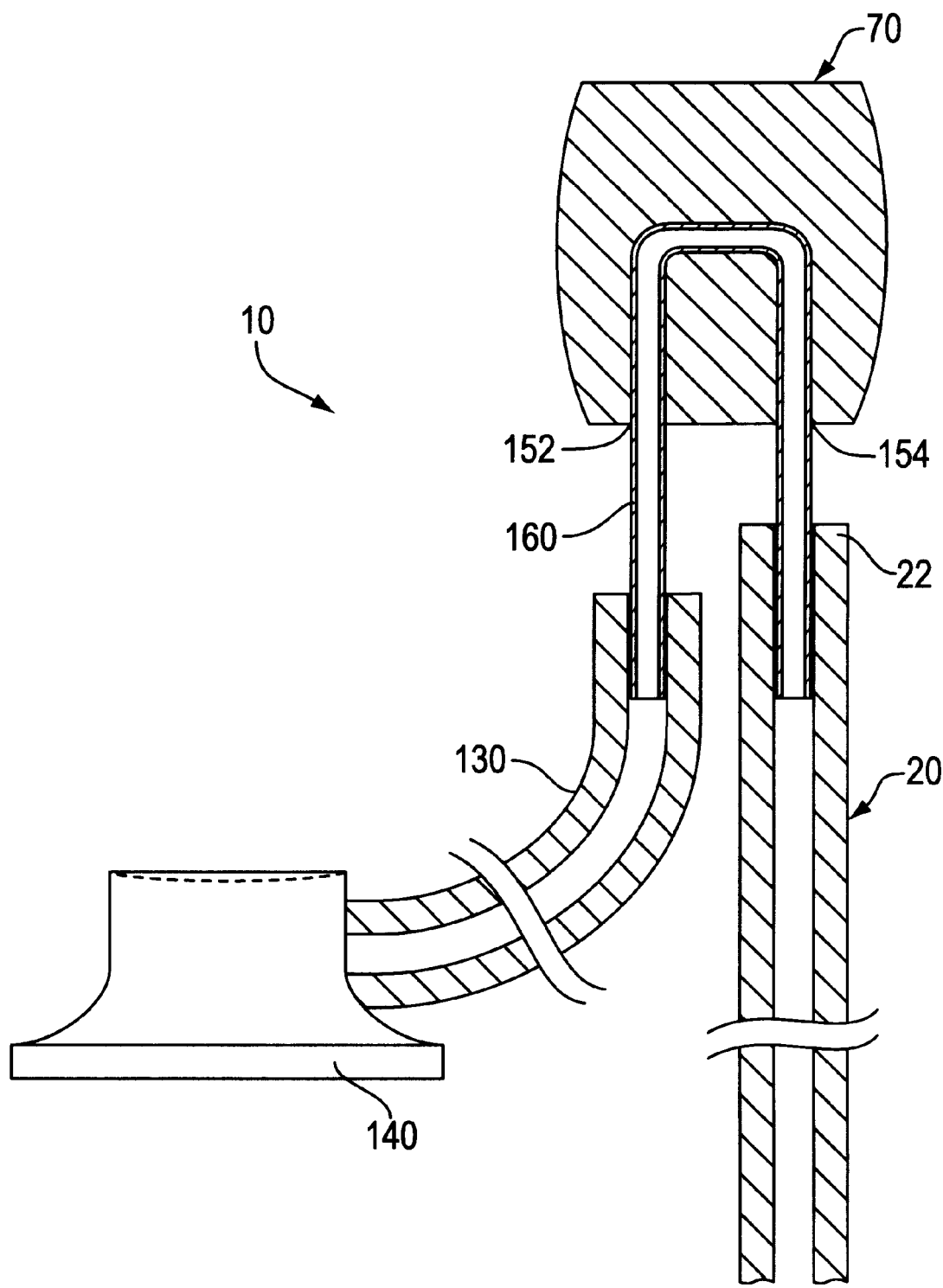
FIG. 13 is a variant of FIG. 12 in which the locating part serves solely as a relay and is not equipped with a means for absorbing axial stresses.
Figure 14:
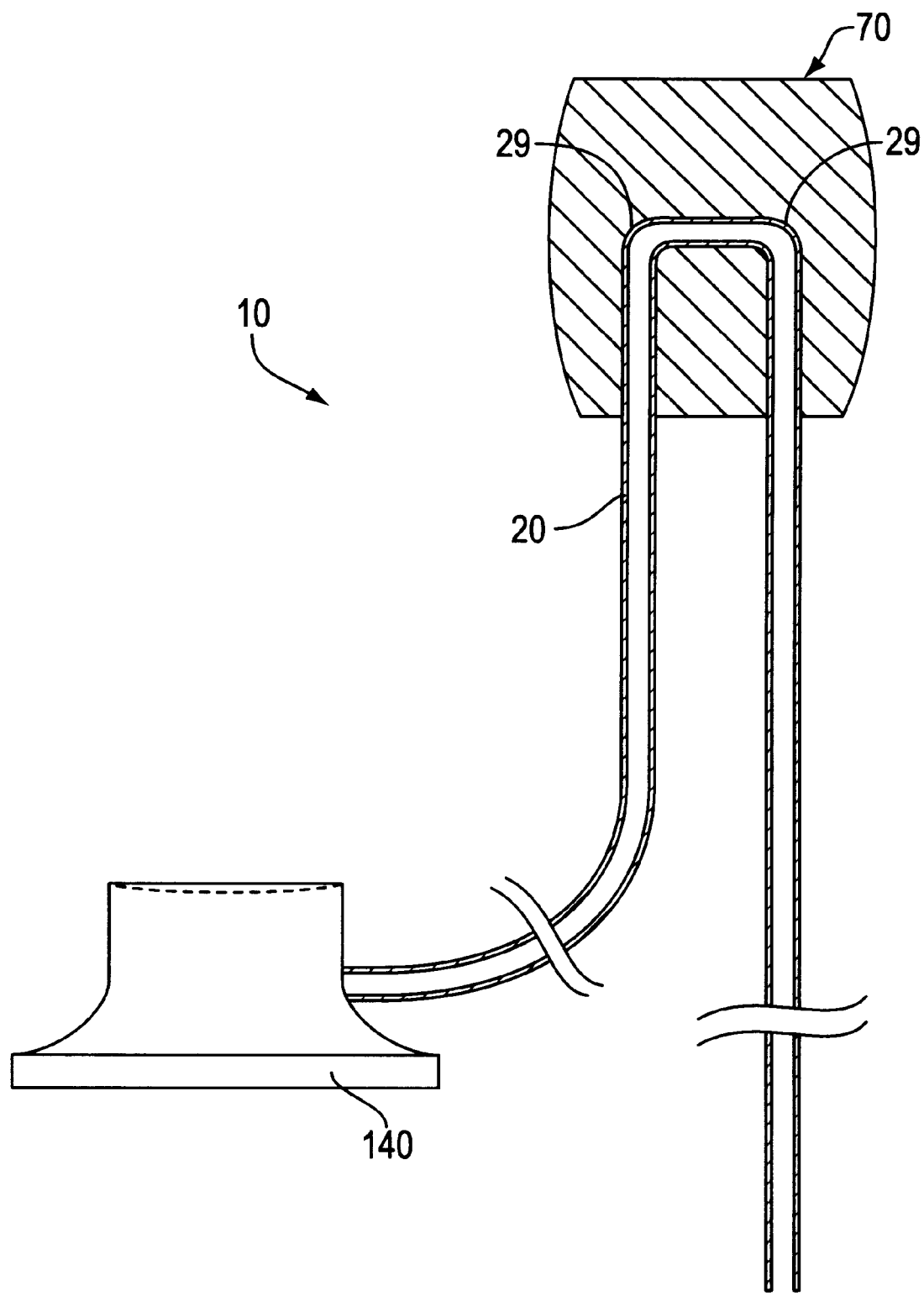
FIG. 14 is a variant of FIG. 13.

FIG. 13 presents a solution to this specific problem. In this solution, the subcutaneous locating part 70 has an internal channel 150 in the form of a "U" (or "L") opening in two orifices 152 and 154 disposed preferably on one and the same face of the part 70, the "U" being capable of being more or less open. A hollow metal tube 160 is inserted in this channel 150 and exits through the two orifices, on one side in order to be connected to the carrier rod 20 and on the other side in order to be connected to a flexible catheter 130 for perfusion placed under the patient's skin and connected to an implantable site 140, as in FIG. 12. The locating part 70 thus represented therefore lacks any means for absorbing stresses and acts solely as a relay in such a way as to permit the transit of a treatment product between the distal end 24 of the carrier rod 20 and the implantable site 140. According to an alternative represented in FIG. 14, the hollow carrier rod 20 can be connected directly to the implantable site 140 whilst passing through the locating part 70. This solution avoids the connections between the different hollow parts (piston rod, flexible catheter, carrier rod), connections which can give way or leak and be sources of problems. Thus the carrier rod 20 has one or more curve(s) 29 (bend) at the level of the locating part. In order to avoid the appearance of folds, this carrier rod 20 is preferably inserted in a sleeve (not shown) or preferably directly in a cavity preformed in the interior of the locating part in such a way as to impose the desired curvature on it. Thus it is always possible to inject a product from the implantable site 140 as far as the distal end 24 of the carrier rod 20 whilst keeping a locating part 70 usable when it is wished to withdraw the temporarily implanted filter 140 from the patient's body.

Naturally, the invention is in no way limited to the embodiments presented above.

Thus it will be possible to provide for the filter 40 to be directly fixed to the distal end 24 of the rod 20 (thus without a pusher) and to dispose the bellows 30 or the assembly consisting of the spring 80 and sheath 90 in the middle part of the rod 20, which will then be is two sections separated by the "absorption means".

It is also possible to envisage the use of this device in other ducts such as the oesophagus or the trachea, or with other types of implants (stent).

The different means for absorbing axial stresses can be combined indiscriminately with one another. In particular, the solution with bellows (or spring) disposed at the distal end of the rod 20 can be combined with a subcutaneous locating part 70 equipped with a means for absorbing axial stresses.

Finally, the bellows 30 (or even possibly the flexible sheath 80) can be equipped with an axial guiding system, such as for example a series of rings made from plastics material or from metal which are crimped inside the bellows and regularly spaced along the pusher rod 50 around which they can slide. Thus the bellows 30 will not come to rub against the pusher rod while curving (bending of the buckling type) as it is compressed, which will avoid premature degradation (wear) of the bellows and/or the occurrence of friction which can hamper the absorption of the stresses or even displace the filter.

What is claimed is:

1. A device for medical use which can be introduced temporarily into a duct of a living human or animal patient's body at a specific implantation location, said device comprising:
    a biocompatible flexible rod which has an axis along which it extends in a rectilinear manner, said rod having a distal end and a proximal end, and
    an implant connected to the distal end of the rod and comprising a radially expansible structure,
    said rod being equipped with at least one means for absorbing axial stresses which is disposed along the axis of said rod and which is distinct therefrom while being connected thereto, whereby the proximal end of the rod is not substantially displaced axially once said rod and said implant have reached the specific implantation location, and
    wherein said means for absorbing axial stresses comprises a piston.

2. A device according to claim 1, wherein the implant is a blood filter.

3. A device according to claim 1, wherein the means for absorbing axial stresses is disposed towards the proximal end of the rod, said proximal end being connected to a subcutaneous part which is locatable by palpation through the patient's skin.

4. A device according to claim 3, wherein the subcutaneous part which is locatable by palpation through the patient's skin is equipped with said means for absorbing axial stresses.

5. A device according to claim 1, wherein the means for absorbing axial stresses further comprises a bellows which can lengthen or shorten axially.

6. A device according to claim 1, wherein the means for absorbing axial stresses further comprises a helical spring.

7. A device according to claim 2, wherein the means for absorbing axial stresses is disposed towards the distal end of the rod.

8. A device according to claim 1, further comprising a guiding and stop system which limits axial displacement of said piston inside the flexible rod.

9. A device according to claim 8, wherein:
    the biocompatible flexible rod is hollow and has an internal diameter,
    the piston has an external diameter, and
    the guiding and stop system comprises:
        a first ring which is connected to the piston, said first ring having an external diameter which is slightly smaller than the internal diameter of the flexible rod, and
        a second ring which is fixed inside the flexible rod, said second ring having an internal diameter which is slightly greater than the external diameter of the piston.

10. A device for medical use which can be introduced temporarily into a duct of a living human or animal body during an implantation period and which can be withdrawn therefrom after the implantation period, said device comprising:
    a biocompatible flexible rod which has an axis along which said rod extends in a rectilinear manner, said rod having a distal end and a proximal end; and
    an implant connected permanently to the distal end of the rod and having a radially expansible structure;
    wherein said rod has at least one means for absorbing axial stresses that is distinct from and connected to the rod, said means being permanently coupled to the implant so as to absorb axial stresses within the rod caused by movement of the human or animal body while said implant is implanted and in a radially expanded state, whereby the implant remains substantially in place at a desired implantation location within said duct as a said human or animal body moves.

* * * * *